(12) United States Patent
Scher et al.

(10) Patent No.: US 6,541,422 B2
(45) Date of Patent: *Apr. 1, 2003

(54) METHOD FOR IMPROVING THE SELECTIVITY OF 1,3-CYCLOHEXANEDIONE HERBICIDE

(75) Inventors: Herbert B. Scher, Moraga, CA (US); Jinling Chen, Randolph, NJ (US)

(73) Assignee: Syngenta Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,639

(22) Filed: May 28, 1999

(65) Prior Publication Data

US 2002/0016491 A1 Feb. 7, 2002

(51) Int. Cl.[7] ............... A01N 55/02; A01N 41/10; A01N 35/06; C07F 19/00; C07C 317/24
(52) U.S. Cl. .............. 504/116; 504/191; 504/190; 504/348; 504/349; 504/350; 544/64; 544/225; 562/430; 564/85; 564/86; 564/92; 564/97; 568/329; 558/412; 558/396; 558/397; 560/12; 560/21

(58) Field of Search ............... 564/85, 86, 87, 564/88, 92, 97; 504/224, 225, 348, 349, 350, 190, 191, 116; 544/64, 225; 560/12, 21; 558/412, 396, 397; 568/329; 562/430

(56) References Cited

U.S. PATENT DOCUMENTS

| 4,285,720 A | 8/1981 | Scher ............... 71/88 |
| 4,780,127 A | 10/1988 | Michaely et al. ............... 71/103 |
| 4,938,796 A | 7/1990 | Buren et al. ............... 71/98 |
| 4,956,129 A | 9/1990 | Scher et al. ............... 264/4.7 |
| 5,006,158 A | 4/1991 | Carter et al. ............... 71/98 |
| 5,089,046 A | 2/1992 | Lee et al. ............... 71/103 |

FOREIGN PATENT DOCUMENTS

| EP | 449385 | * | 3/1991 |
| WO | 97/27748 | | 8/1997 |

* cited by examiner

*Primary Examiner*—Sabiha Qazi
(74) *Attorney, Agent, or Firm*—Wiliam A. Teoli, Jr.; Rose M. Allen

(57) ABSTRACT

A method of selectively controlling undesirable vegetation in crops by using a postemergent application of an herbicidally effective amount of a metal chelate of a 2-(substituted benzoyl)-1,3-cyclohexanedione compound to the locus of such undesirable vegetation.

30 Claims, No Drawings

METHOD FOR IMPROVING THE SELECTIVITY OF 1,3-CYCLOHEXANEDIONE HERBICIDE

FIELD OF THE INVENTION

The present invention is directed to the use of metal chelates as a delivery system to improve the selectivity of 2-(substituted benzoyl)-1,3-cyclohexanedione compounds as post-emergence herbicides in crops.

BACKGROUND OF THE INVENTION

The protection of crops from weeds and other undesirable vegetation which inhibit crop growth is a constantly recurring problem in agriculture. To help combat this problem researchers in the field of synthetic chemistry have produced an extensive variety of chemicals and chemical formulations effective in the control of such unwanted growth. Chemical herbicides of many types have been disclosed in the literature and a large number are in commercial use.

Unfortunately, many of such herbicides exhibit phytotoxicity to the desired crop as well as to the weeds sought to be controlled. Thus, there is a long-standing need for selective herbicides which will control frequently occurring weeds but which will not adversely affect the crop plants when applied at herbicidally effective levels.

U.S. Pat. Nos. 4,780,127, 4,938,796, 5,006,158 and 5,089,046 disclose 2-(substituted benzoyl)-1,3-cyclohexanedione compounds having the general structure:

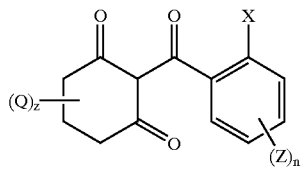

(I)

wherein X, Q and Z have the meanings set forth hereinafter. These dione compounds have proved to be effective pre-emergent and postemergent herbicides against a wide variety of grasses, broadleaf weeds and sedges. Moreover, PCT Application No. 97/27748 discloses that metal chelates of 2-(substituted benzoyl)-1,3-cyclohexanedione compounds have proved to be chemically stable for long periods of time under normal as well as extreme temperature conditions.

The parent cyclohexanedione exhibits a substantial phytotoxic effect. In contrast, it has now been discovered that metal chelates of 2-(substituted benzoyl)-1,3-cyclohexanedione compounds will effectively control a broad range of weeds without exhibiting any substantial phytotoxic effect on the crop itself.

SUMMARY OF THE INVENTION

The present invention is directed to methods of selectively controlling weeds and other undesirable vegetation in a given crop such as wheat. In one embodiment of this invention, the method comprises the postemergent application of an herbicidally effective amount of a metal chelate of a 2-(substituted benzoyl)-1,3-cyclohexanedione to the locus of such weeds and other vegetation. In another embodiment of this invention, the method comprises the postemergent application of an herbicidally effective amount of a metal chelate of a 2-(substituted benzoyl)-1,3-cyclohexanedione to the locus of such weeds and other vegetation, said metal chelate having been formulated as a microcapsule.

As is employed herein, the term "herbicide" is used to denote a compound which controls or modifies the growth of plants. The term "herbicidally effective amount" is used to indicate the quantity of such compound which is capable of producing a controlling or modifying effect. Controlling or modifying effects include all deviations from natural development, for example: killing, retardation, leaf burn, albinism, dwarfing, and the like. The term "plants" refers to all physical parts of a plant, including seeds, seedlings, saplings, roots, tubers, stems, stalks, foliage, and fruits.

DETAILED DESCRIPTION OF THE INVENTION

The present invention relates to the use of metal chelates of herbicidal dione compounds to selectively control weeds and other undesirable vegetation in a given crop such as wheat. These herbicidal dione compounds have the general formula (I):

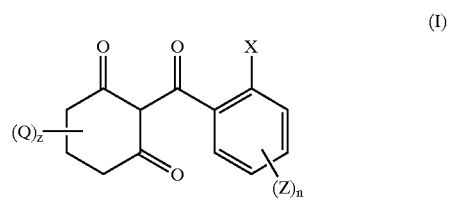

(I)

wherein X represents a halogen atom; a straight- or branched-chain alkyl or alkoxy group containing up to six carbon atoms which is optionally substituted by one or more groups —$OR^1$ or one or more halogen atoms; or a group selected from nitro, cyano, —$CO_2$ $R^2$—$S(O)_mR^1$, —$O(CH_2)_m$ $OR^1$, —$COR^2$, —$OSO_2R^4$, —$NR^2R^3$, —$SO_2NR^2R^3$, —$CONR^2R^3$ and —$CSNR^2R^3$;

$R^1$ represents a straight- or branched-chain alkyl group containing up to six carbon atoms which is optionally substituted by one or more halogen atoms;

$R^2$ and $R^3$ each independently represents a hydrogen atom; or a straight- or branched-chain alkyl group containing up to six carbon atoms which is optionally substituted by one or more halogen atoms;

$R^4$ represents a straight- or branched-chain alkyl, alkenyl or alkynyl group containing up to six carbon atoms optionally substituted by one or more halogen atoms; or a cycloalkyl group containing from three to six carbon atoms;

each Z independently represents halo, nitro, cyano, $S(O)_m$ $R^5$, $OS(O)_mR^5$, $(C_1$–$C_6)$alkyl, $(C_1$–$C_6)$alkoxy, $(C_1$–$C_6)$ haloalkyl, $(C_1$–$C_6)$haloalkoxy, carboxy, $(C_1$–$C_6)$ alkylcarbonyloxy, $(C_1$–$C_6)$alkoxycarbonyl, $(C_1$–$C_6)$ alkylcarbonyl, amino, $(C_1$–$C_6)$alkylamino, $(C_1$–$C_6)$ dialkylamino having independently the stated number of carbon atoms in each alkyl group, $(C_1$–$C_6)$ alkylcarbonylamino, $(C_1$–$C_6)$alkoxycarbonylamino, $(C_1$–$C_6)$alkylaminocarbonylamino, $(C_1$–$C_6)$ dialkylaminocarbonylamino having independently the stated number of carbon atoms in each alkyl group, $(C_1$–$C_6)$alkoxycarbonyloxy, $(C_1$–$C_6)$ alkylaminocarbonyloxy, $(C_1$–$C_6)$ dialkylaminocarbonyloxy, phenylcarbonyl, substituted phenylcarbonyl, phenylcarbonyloxy, substituted phenylcarbonyloxy, phenylcarbonylamino, substituted phenylcarbonylamino, phenoxy or substituted phenoxy;

$R^5$ represents cyano; —$COR^6$; —$CO_2R^6$; or —$S(O)_mR^7$;

$R^6$ represents hydrogen or straight- or branched-chain alkyl group containing up to six carbon atoms;

$R^7$ represents $(C_1-C_6)$alkyl, $(C_1-C_6)$haloalkyl, $(C_1-C_6)$ cyanoalkyl $(C_3-C_8)$cycloalkyl optionally substituted with halogen, cyano or $(C_1-C_4)$alkyl; or phenyl optionally substituted with one to three of the same or different halogen, nitro, cyano, $(C_1-C_4)$haloalkyl, $(C_1-C_4$ alkyl, $(C_1-C_4)$alkoxy or —S(O)$_m$R$^8$;

$R^8$ represents $(C_1-C_4)$alkyl, $(C_1-C_4)$alkyl substituted with halogen or cyano, phenyl or benzyl;

each Q independently represents $C_1-C_4$ alkyl or —CO$_2$R$^9$ wherein $R^9$ is $C_1-C_4$ alkyl;

m is zero, one or two;

n is zero or an integer from one to four;

r is one, two or three; and z is 0 or an integer from 1 to 6.

As used herein, the terms "halogen" and "halo" include fluorine, chlorine, bromine and iodine atoms. In polyhalogenated groups, the halogens may be the same or different. The term "substituted" in terms of "substituted phenylcarbonyl," "substituted phenylcarbonyloxy," "substituted phenylcarbonylamino" and "substituted phenoxy" means having one to five substituents, which may be the same or different, selected from the following: halo, nitro, cyano, $S(O)_mR^2$, $(C_1-C_6)$alkyl, $(C_1-C_6)$alkoxy, $(C_1-C_6)$ haloalkyl, $(C_1-C_6)$haloalkoxy, carboxy, $(C_1-C_6)$ alkylcarbonyloxy, $(C_1-C_6)$alkylcarbonyl, $(C_1-C_6)$ alkoxycarbonyl, $(C_1-C_6)$alkylcarbonylamino, amino, $(C_1-C_6)$alkylamino and $(C_1-C_6)$dialkylamino having independently the stated number of carbon atoms in each group.

The 2-(substituted benzoyl)-1,3-cyclohexanedione compounds of formula I are described, inter alia, in U.S. Pat. Nos. 4,780,127, 4,938,796, 5,006,158 and 5,089,046, the disclosures of which are incorporated herein by reference. Herbicidal 2-(substituted benzoyl)-1,3-cyclohexanedione compounds for use in this invention may be prepared by the methods described in the aforementioned patent publications, or by the application and adaptation of known methods used or described in the chemical literature.

2-(substituted benzoyl)-1,3-cyclohexanedione compounds especially useful in the present invention include those in which z is zero; X is chloro, bromo, nitro, cyano, $C_1-C_4$ alkyl, —CF$_3$, —S(O)$_m$R$^1$ or —OR$^1$; n is one or two; and each Z is independently chloro, bromo, nitro, cyano, $C_1-C_4$ alkyl, —CF$_3$, —OR$^1$, —OS(O)$_m$R$^5$ or —S(O)$_m$R$^5$. Examples of preferred cyclohexanedione compounds are 2-(2'-nitro-4'-methylsulfonylbenzoyl)-1,3-cyclohexanedione, 2-(2'-nitro-4'-methylsulfonyloxybenzoyl)-1,3-cyclohexanedione and 2-(2'-chloro-4'-methylsulfonylbenzoyl)-1,3-cyclohexanedione.

Compounds of formula (I) may exist in enolic tautomeric forms that may give rise to geometric isomers. Furthermore, in certain cases, the various substituents may contribute to optical isomerism and/or stereoisomerism. All such forms are embraced within compounds useful in the present invention.

Metal chelates of 2-(substituted benzoyl)-1,3-cyclohexanedione compounds of formula I are described, inter alia, in PCT Application No. 97/27748, the disclosures of which are incorporated herein by reference. Metal chelates of 2-(substituted benzoyl)-1,3-cyclohexanedione compounds have the general structure:

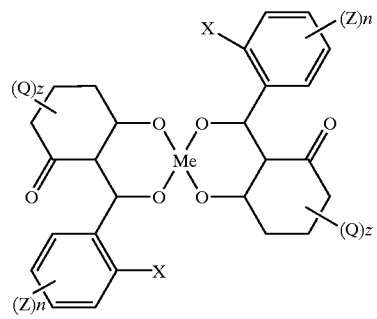

(II)

wherein X, Q and Z have the meanings set forth above, and Me represents a di- or trivalent metal ion such as $Cu^{+2}$, $Co^{+2}$, $Zn^{+2}$, $Ni^{+2}$, $Ca^{+2}$, $Al^{+3}$, $Ti^{+3}$ and $Fe^{+3}$.

Herbicidal metal chelates of 2-(substituted benzoyl)-1,3-cyclohexanedione compounds for use in this invention may be prepared by the methods described in the aforementioned PCT application, or by the application and adaptation of known methods used or described in the chemical literature.

Metal ions which may be useful in forming the metal chelate compounds of the present invention include di- or trivalent metal ions such as $Cu^{+2}$, $Co^{+2}$, $Zn^{+2}$, $Ni^{+2}$, $Ca^{+2}$, $Al^{+3}$, $Ti^{+3}$ and $Fe^{+3}$. The selection of a particular metal ion to form the metal chelate compound will depend upon the dione compound to be chelated and the strength of the metal chelate complex. Without being bound by theory, it appears as if the strength of the metal chelate complex is directly related to the release rate of the triketone from the metal chelate complex, which in turn is related to the selectivity of the metal chelate compounds of this invention. Those skilled in the art will be able to readily determine the appropriate metal ion for use with a specific dione compound without undue experimentation. The preferred metal ions are divalent transition metal ions, particularly $Cu^{+2}$, $Ni^{+2}$, $Zn^{+2}$ and $Co^{+2}$, with $Cu^{+2}$ being especially preferred.

Any appropriate salt which would be a source of a di- or trivalent metal ion may be used to form the metal chelate of the dione compound in accordance with this invention. Particularly suitable salts include: chlorides, sulfates, nitrates, carbonates, phosphates and acetates.

It also has been found that the stability and the activity of the herbicidal metal chelate compositions of the present invention is pH dependent. The pH of the metal chelate compositions should be between about 2 and about 10, preferably between about 3 and about 7. Generally, it is believed that for $Cu^{+2}$ chelate compositions the pH should be between about 4 and 6; for $Co^{+2}$ between about 3 and 5; and for $Ni^{+2}$ and $Zn^{+2}$ about 5. The optimum pH for a particular metal chelate composition can be determined using routine experimental techniques.

The metal chelate of the herbicidal 2-(substituted benzoyl)-1,3-cyclohexanedione compounds can be formulated in the same manner in which herbicides are generally formulated. The choice of formulation and mode of application for any given herbicidal compound may affect its activity, and selection must be made accordingly. Herbicidal compositions may thus be formulated as water dispersible granules, as wettable powders, as powders or dusts, as suspensions, or as controlled release forms such as microcapsules. The formulation of the metal chelate of the herbicidal 2-(substituted benzoyl)-1,3-cyclohexanedione compounds for use in this invention may be prepared by the methods described in the aforementioned patent application or by the application and adaptation of known methods used or described in the chemical literature. Processes for microencapsulating the herbicidal composition specifically have been described in U.S. Pat. Nos. 4,285,720 and 4,956,129 and U.S. application Ser. No. 08/354,409, and may also be prepared by the application and adaptation of known methods used or described in the chemical literature. The object of the formulation, however, is to apply the compositions to the locus where control is desired by a convenient method (i.e., postemergent application). The "locus" is intended to include soil, as well as established vegetation.

Formulations containing the metal chelates of the herbicidal dione compounds of formula (I) can be applied by conventional methods to the areas where control is desired. The formulations containing an herbicidal metal chelate according to the invention can also be produced as premixes with other herbicides, or can be tank-mixed with one or more additional herbicidal or other agricultural compositions. Specific examples of other herbicides which may be incorporated in an herbicidal formulation with the metal chelates according the invention include acetanilides, tralkoxydim, bromoxynil and its esters, thiafluamide, MCPA and its esters, 2,4-D and its esters, and fluroxypyr meptyl.

In the practice of the present invention, the metal chelate of the herbicidal 2-(substituted benzoyl)-1,3-cyclohexanedione compounds is applied postemergent to the locus of the undesirable vegetation to be controlled. Application rates will depend on the particular plant species and degree of control desired. In general, application rates of between about 5 and about 500 g/ha may be employed.

The following examples are for illustrative purposes only and are not intended as necessarily representative of the overall testing performed and are not intended to limit the invention in any way.

SPECIFIC EMBODIMENTS OF THE INVENTION

Example 1

All of the metal chelate compounds used in the 1,3-cyclohexanedione formulations of this example were prepared using a mix and mill process except for Formulation C which was formulated using a precipitation process. Both the mix and mill process and the precipitation process are described in more detail in PCT Application Ser. No. 97/27748, the disclosure of which has been incorporated herein by reference.

Twelve days after the seeds were sown in aluminum flats (containing soil comprising 2 parts sandy loam to 1 part peat), the 1,3-cyclohexanedione suspension formulations (at the rates listed in Table I below) were applied postemergence to the following plant species: *Galium aparine* (catchweed bedstraw) ("GALAP"); *Chenopodium album* (lambsquarters) ("CHEAL"); *Matricaria inodora* (scentless flase chamomile) ("MATIN"); and wheat.

The flats were placed in a greenhouse and evaluated 6 and 21 days after application ("DAA"). Injury was evaluated as percent control, with percent control being the total injury to the plants due to all factors including: Inhibited emergence, stunting, malformation, albinism, chlorisis, and other types of plant injury. The control rating range from 0 to 100 percent, where 0% represents no effect with growth equal to the untreated control and where 100% represents a complete kill.

The results observed (as a mean of 3 replications) are summarized in Table I below.

TABLE I

Bioactivity of Various Metal Chelates of 1,3-Cyclohexanedione Formulations

| Formulation | Molar Ratio Dione/Metal | Appl. Rate g a.i./ha | Phytotoxicity to Wheat, % | | Weed Control Activity, % | | |
|---|---|---|---|---|---|---|---|
| | | | 6 days | 21 days | GALAP 21 days | CHEAL 21 days | MATIN 21 days |
| Control 1 (Unchelated) | | 12.5 | 38 | 10 | 75 | 100 | 99 |
| | | 25 | 45 | 14 | 54 | 100 | 100 |
| | | 50 | 53 | 22 | 99 | 100 | 100 |
| | | 100 | 65 | 58 | 100 | 100 | 100 |
| Formulation A (Cu Chelate) | 2/5 | 12.5 | 0 | 0 | 64 | 100 | 0 |
| | | 25 | 2 | 0 | 75 | 100 | 44 |
| | | 50 | 2 | 0 | 83 | 100 | 72 |
| | | 100 | 2 | 4 | 98 | 100 | 85 |
| Formulation B (Cu Chelate) | 2/1 | 12.5 | 0 | 0 | 83 | 100 | 18 |
| | | 25 | 2 | 0 | 87 | 100 | 45 |
| | | 50 | 0 | 0 | 84 | 100 | 73 |
| | | 100 | 2 | 6 | 99 | 100 | 90 |
| Formulation C (Cu Chelate) | 2/1 | 12.5 | 0 | 0 | 93 | 100 | 84 |
| | | 25 | 0 | 0 | 94 | 100 | 79 |
| | | 50 | 0 | 0 | 68 | 100 | 100 |
| | | 100 | 8 | 7 | 99 | 100 | 100 |
| Formulation D (Co Chelate) | 2/5 | 12.5 | 5 | 0 | 44 | 100 | 100 |
| | | 25 | 8 | 2 | 61 | 100 | 88 |
| | | 50 | 25 | 10 | 84 | 100 | 55 |
| | | 100 | 33 | 14 | 100 | 100 | 99 |
| Formulation E (Co Chelate) | 2/1 | 12.5 | 23 | 2 | 63 | 100 | 99 |
| | | 25 | 33 | 2 | 66 | 100 | 100 |
| | | 50 | 38 | 20 | 94 | 100 | 100 |
| | | 100 | 43 | 38 | 99 | 100 | 100 |

TABLE I-continued

Bioactivity of Various Metal Chelates of 1,3-Cyclohexanedione Formulations

| Formulation | Molar Ratio Dione/Metal | Appl. Rate g a.i./ha | Phytotoxicity to Wheat, % 6 days | Phytotoxicity to Wheat, % 21 days | Weed Control Activity, % GALAP 21 days | Weed Control Activity, % CHEAL 21 days | Weed Control Activity, % MATIN 21 days |
|---|---|---|---|---|---|---|---|
| Formulation F (Zn Chelate) | 2/5 | 12.5 | 20 | 2 | 66 | 100 | 100 |
|  |  | 25 | 28 | 8 | 71 | 100 | 100 |
|  |  | 50 | 35 | 17 | 99 | 100 | 93 |
|  |  | 100 | 40 | 18 | 98 | 100 | 100 |
| Formulation G (Zn Chelate) | 2/1 | 12.5 | 28 | 3 | 64 | 100 | 65 |
|  |  | 25 | 35 | 10 | 89 | 100 | 99 |
|  |  | 50 | 40 | 19 | 84 | 100 | 100 |
|  |  | 100 | 45 | 35 | 100 | 100 | 100 |
| Formulation H (Ni Chelate) | 2/5 | 12.5 | 20 | 3 | 85 | 100 | 100 |
|  |  | 25 | 30 | 3 | 59 | 100 | 100 |
|  |  | 50 | 40 | 9 | 100 | 100 | 100 |
|  |  | 100 | 45 | 31 | 98 | 100 | 100 |
| Formulation I (Ca Chelate) | 2/5 | 12.5 | 30 | 6 | 78 | 100 | 100 |
|  |  | 25 | 40 | 9 | 83 | 100 | 100 |
|  |  | 50 | 45 | 25 | 100 | 100 | 100 |
|  |  | 100 | 53 | 48 | 94 | 100 | 100 |

From these results, it is clear that the phytotoxicity of the 1,3-cyclohexanedione formulations to wheat was reduced by chelation. In contrast, however, the herbicidal activity of the 1,3-cyclohexanedione formulations on the weeds and other undesirable vegetation was only slightly affected by chelation. In addition, it is also apparent from these results that the activity of the 1,3-cyclohexanedione formulation varied depending on the metal ion used to form the metal chelate compound.

Example 2

The metal chelate compounds used in the 1,3-cyclohexanedione suspension formulations of this example were prepared using the mix and mill process as described in Example 1. Moreover, a procedure essentially identical to that described in Example 1 was employed for the postemergent application of the 1,3-cyclohexanedione suspension formulations (at the rates listed in Table II below) to aluminum flats containing the following plant species: CHEAL; *Amaranthus retroflexus* (redroot pigweed) ("AMARE"); *Polygonum convolvulus* (wild buckwheat) ("POLCO"); *Brassica kaber* (wild mustard)("SINAR"); *Thlaspi arventse* (field pennycress)("THLAR"); *Brassica canpestris* (oilseed rape)("BRSNN"); wheat ("TRZAS"); and barley ("HORVS"). Injury was evaluated at 8 and 32 DAA.

The results observed (as a mean of 4 replications) are summarized in Table II below.

TABLE II

Comparison of Activity and Phytotoxicity of Chelated and Unchelated 1,3-Cyclohexanedione (a.i.) Formulations

| Formulation | Rate g a.i./ha | Phytotoxicity to Wheat (TRZAS) TRZAS 8 days | Phytotoxicity to Wheat (TRZAS) TRZAS 32 days | Phytotoxicity to Barley (HORVS), % HORVS 8 days | Phytotoxicity to Barley (HORVS), % HORVS 32 days | Weed Control Activity, % (32 days) AMARE 32 days | Weed Control Activity, % (32 days) BRSNN 32 days | Weed Control Activity, % (32 days) CHEAL 32 days | Weed Control Activity, % (32 days) POLCO 32 days | Weed Control Activity, % (32 days) SINAR 32 days | Weed Control Activity, % (32 days) THLAR 32 days |
|---|---|---|---|---|---|---|---|---|---|---|---|
| Control 2 (Unchelated) | 3.125 | 4 | 1 | 0 | 0 | 80 | 69 | 100 | 4 | 92 | 85 |
|  | 6.25 | 14 | 5 | 4 | 0 | 88 | 86 | 100 | 53 | 99 | 91 |
|  | 12.5 | 19 | 1 | 6 | 0 | 97 | 89 | 100 | 81 | 98 | 99 |
|  | 25 | 24 | 12 | 6 | 0 | 98 | 97 | 100 | 94 | 97 | 100 |
|  | 50 | 34 | 15 | 11 | 4 | 100 | 100 | 100 | 100 | 100 | 100 |
|  | 100 | 44 | 59 | 18 | 6 | 100 | 100 | 100 | 100 | 100 | 100 |
| Formulation J (Cu Chelate) | 6.25 | 0 | 0 | 0 | 1 | 100 | 90 | 100 | 100 | 100 | 99 |
|  | 12.5 | 0 | 0 | 0 | 1 | 98 | 82 | 100 | 98 | 99 | 94 |
|  | 25 | 0 | 0 | 0 | 0 | 99 | 89 | 100 | 66 | 100 | 99 |
|  | 50 | 0 | 0 | 0 | 1 | 100 | 89 | 100 | 88 | 100 | 100 |
|  | 100 | 4 | 34 | 1 | 3 | 100 | 95 | 100 | 100 | 100 | 100 |
|  | 200 | 11 | 64 | 0 | 4 | 100 | 100 | 100 | 100 | 99 | 100 |

These data indicate that the copper chelate of 2-(substituted benzoyl)-1,3-cyclohexanedione, Formulation J, showed an 16X increase in wheat selectivity at early assessment compared to the unchelated formulation (Control 2). Weed control activity of the copper chelate formulation was approximately the same as that of the unchelated formulation.

Example 3

The metal chelate compounds used in the 1,3-cyclohexanedione formulations of this example were prepared using the mix and mill process as described in Example 1. Control 3 and Formulation K were formulated as suspension formulations and Formulation L was formulated as microcapsules.

Employing a procedure essentially identical to that described in Example 1, the 1,3-cyclohexanedione formulations were applied postemergence at the rates listed in Table III below to aluminum flats containing the following plant species: AMARE, BRSNS, POLCO, SINAR and TRZAS. Injury was evaluated at 6 and 22 DAA.

The results observed (as a mean of 4 replications) are summarized in Table III below.

TABLE III

Comparison of Activity and Phytotoxicity of Unchelated, Chelated and Microencapsulated 1,3-Cyclohexandedione (a.i.) Formulations

| Formulation | Rate g a.i./ha | Phytotoxicity to Wheat, % | | | | Weed Control Activity, % | | | |
|---|---|---|---|---|---|---|---|---|---|
| | | TRZAS(K) | | TRZAS(R) | | AMARE | BRSNN | POLCO | SINAR |
| | | 6 days | 22 days | 6 days | 22 days | 22 days | 22 days | 22 days | 22 days |
| Control 3 | 2.5 | — | — | — | — | 56 | 38 | 48 | 87 |
| (Unchelated) | 5 | — | — | — | — | 85 | 48 | 65 | 85 |
| | 10 | — | — | — | — | 90 | 81 | 83 | 97 |
| | 20 | 23 | 10 | 26 | 8 | 97 | 88 | 97 | 100 |
| | 40 | 29 | 9 | 40 | 18 | 99 | 96 | 88 | 100 |
| | 80 | 34 | 18 | 50 | 25 | — | — | — | — |
| | 160 | 60 | 58 | 58 | 59 | — | — | — | — |
| | 320 | 61 | 80 | 61 | 80 | — | — | — | — |
| Formulation K | 2.5 | — | — | — | — | 41 | 65 | 55 | 97 |
| (Cu Chelate) | 5 | — | — | — | — | 72 | 56 | 67 | 92 |
| | 10 | — | — | — | — | 61 | 65 | 62 | 93 |
| | 20 | 4 | 3 | 16 | 14 | 88 | 73 | 89 | 95 |
| | 40 | 10 | 17 | 6 | 31 | 97 | 90 | 92 | 96 |
| | 80 | 0 | 8 | 12 | 21 | — | — | — | — |
| | 160 | 6 | 33 | 7 | 33 | — | — | — | — |
| | 320 | 39 | 74 | 49 | 69 | — | — | — | — |
| Formulation L | 2.5 | — | — | — | — | 20 | 39 | 25 | 88 |
| (Cu Chelate/ | 5 | — | — | — | — | 26 | 10 | 28 | 78 |
| Microcapsule) | 10 | — | — | — | — | 45 | 16 | 45 | 88 |
| | 20 | 1 | 1 | 6 | 5 | 75 | 31 | 66 | 99 |
| | 40 | 0 | 3 | 1 | 6 | 95 | 71 | 84 | 98 |
| | 80 | 1 | 13 | 0 | 10 | — | — | — | — |
| | 160 | 0 | 38 | 4 | 33 | — | — | — | — |
| | 320 | 39 | 66 | 15 | 58 | — | — | — | — |

The above data indicates that the copper chelate of 2-(substituted benzoyl)-1,3-cyclohexanedione (Formulation K) showed improved selectivity over the unchelated formulation (Control 3). These data also indicate that the selectivity of the copper chelate of 2-(substituted benzoyl)-1,3-cyclohexanedione was further improved by microencapsulation (Formulation L).

The foregoing description and example are for the purpose of illustration only and does not limit the scope of protection which should be accorded this invention.

What is claimed is:

1. A method of selectively controlling undesirable vegetation in a desired crop comprising applying postemergence an herbicidally effective amount of a metal chelate of 2-(2'-nitro4'-methylsulfonylbenzoyl)-1,3-cyclohexanedione to the locus of the undesirable vegetation and the desired crop to selectively control the undesirable vegetation.

2. The method of claim 1, wherein the metal is copper, cobalt, zinc, nickel, aluminum, calcium, titanium, or iron.

3. The method of claim 1, wherein the metal is copper.

4. The method of claim 1, wherein the pH of the metal chelate of the 2-(2'-nitro-4'-methylsulfonylbenzoyl)-1,3-cyclohexanedione is between about 2 and 10.

5. The method of claim 3, wherein the pH of the copper chelate of the 2-(2'-nitro-4'-methylsulfonylbenzoyl)-1,3-cyclohexanedione is between 4 and 6.

6. The method of claim 1, wherein the metal chelate of the 2-(2'-nitro-4'-methylsulfonylbenzoyl)-1,3-cyclohexanedione is microencapsulated.

7. The method of claim 2, wherein the desired crop is wheat.

8. The method of claim 2, wherein the undesirable vegetation is one or more of *Galium aparine*, *Chenopodium album*, *Matricaria inodora*, *Amaranthus retroflexus*, *Polygonum convolvulus*, *Brassica kaber*, *Thlaspi arventse*, and *Brassica canpestris*.

9. The method of claim 2, wherein the metal chelate exhibits low phytotoxicity to the desired crop.

10. The method of claim 1, wherein the herbicidally effective amount is between about 5 and about 500 g/ha.

11. A method of selectively controlling undesirable vegetation in a desired crop comprising applying postemergence an herbicidally effective amount of a metal chelate of 2-(2'-nitro-4'-methylsulfonyloxybenzoyl)-1,3- cyclohexanedione to the locus of the undesirable vegetation and the desired crop to selectively control the undesirable vegetation.

12. The method of claim 11, wherein the metal is copper, cobalt, zinc, nickel, aluminum, calcium, titanium, or iron.

13. The method of claim 11, wherein the metal is copper.

14. The method of claim 11, wherein the pH of the metal chelate of the 2-(2'-nitro-4'-methylsulfonyloxybenzoyl)-1,3-cyclohexanedione is between about 2 and 10.

15. The method of claim 13, wherein the pH of the copper chelate of the 2-(2'-nitro-4'-methylsulfonyloxybenzoyl)-1,3-cyclohexanedione is between 4 and 6.

16. The method of claim 11, wherein the metal chelate of the 2-(2'-nitro-4'-methylsulfonyloxybenzoyl)-1,3-cyclohexanedione is microencapsulated.

17. The method of claim 11, wherein the desired crop is wheat.

18. The method of claim 11, wherein the undesirable vegetation is one or more of *Galium aparine, Chenopodium album, Matricaria inodora, Amaranthus retroflexus, Polygonum convolvulus, Brassica kaber, Thlaspi arventse,* and *Brassica canpestris*.

19. The method of claim 11, wherein the metal chelate exhibits low phytotoxicity to the desired crop.

20. The method of claim 11, wherein the herbicidally effective amount is between about 5 and about 500 g/ha.

21. A method of selectively controlling undesirable vegetation in a desired crop comprising applying postemergence an herbicidally effective amount of a metal chelate of 2-(2'-chloro-4'-methylsulfonylbenzoyl)-1,3-cyclohexanedione to the locus of the undesirable vegetation and the desired crop to selectively control the undesirable vegetation.

22. The method of claim 21, wherein the metal is copper, cobalt, zinc, nickel, aluminum, calcium, titanium, or iron.

23. The method of claim 21, wherein the metal is copper.

24. The method of claim 21, wherein the pH of the metal chelate of the 2-(2'-chloro-4'-methylsulfonylbenzoyl)-1,3-cyclohexanedione is between about 2 and 10.

25. The method of claim 23, wherein the pH of the copper chelate of the 2-(2'-chloro-4'-methylsulfonylbenzoyl)-1,3-cyclohexanedione is between 4 and 6.

26. The method of claim 21, wherein the metal chelate of the 2-(2'-chloro-4'-methylsulfonylbenzoyl)-1,3-cyclohexanedione is microencapsulated.

27. The method of claim 21, wherein the desired crop is wheat.

28. The method of claim 21, wherein the-undesirable vegetation is one or more of *Galium aparine, Chenopodium album, Matricaria inodora, Amaranthus retroflexus, Polygonum convolvulus, Brassica kaber, Thlaspi arventse,* and *Brassica canpestris*.

29. The method of claim 21, wherein the metal chelate exhibits low phytotoxicity to the desired crop.

30. The method of claim 21, wherein the herbicidally effective amount is between about 5 and about 500 g/ha.

* * * * *